United States Patent [19]

Exconde et al.

[11] Patent Number: 5,496,310
[45] Date of Patent: Mar. 5, 1996

[54] ENDOSCOPIC CHOLANGIOGRAM GUIDE INSTRUMENT AND METHOD OF USE

[76] Inventors: Primo D. Exconde, 450 N. Pickaway St., Circleville, Ohio 43113; John S. Thomas, 42 E. Prescott St., Columbus, Ohio 43215

[21] Appl. No.: 315,866

[22] Filed: Sep. 30, 1994

[51] Int. Cl.$^6$ .................................................. A61B 17/28
[52] U.S. Cl. .......................................... 606/205; 606/206
[58] Field of Search .................................... 606/167, 205, 606/206, 207, 208, 209; 604/158, 159, 164, 264, 280

[56] References Cited

U.S. PATENT DOCUMENTS

| | | | |
|---|---|---|---|
| 4,578,058 | 3/1986 | Grandon | 604/27 |
| 5,217,460 | 6/1993 | Knoepfler | 606/207 |
| 5,224,931 | 7/1993 | Kumar | 606/205 |
| 5,224,954 | 7/1993 | Watts | 606/205 |
| 5,234,443 | 8/1993 | Phan | 606/205 |
| 5,350,384 | 9/1994 | Clement | 606/206 |
| 5,352,237 | 10/1994 | Rodak | 606/205 |

*Primary Examiner*—Michael A. Brown
*Attorney, Agent, or Firm*—Mueller and Smith

[57] ABSTRACT

A guide instrument for cannulating a biliary duct with a flexible catheter, and a method of using the same as part of a laparoscopic cholangiographic surgical procedure. The guide instrument is provided as having a grasping forceps component formed of an elongate shaft extending along a longitudinal axis between a first and a second end. A pair of jaws are positioned at the first end of the shaft and are mutually pivotally coupled thereat for movement between an opened and a closed orientation for selectively grasping the duct. An actuator positioned at the second end of the shaft is coupled in a drive relationship with the jaws for moving the jaws between the opened and closed orientations. An elongate, generally cylindrical guide tube is slidably supported along the longitudinal axis of the elongate shaft and is formed as having an internal catheter channel therethrough. The catheter channel has a central axis which is spaced radially from the longitudinal axis, and is provided to extend between an input end for receiving the catheter and an output end for expressing the catheter from the guide tube. The guide tube is rotatable about the longitudinal axis to define with the central axis of the catheter channel a first confrontation radius for presenting the catheter expressed from the output end of the catheter channel to the biliary duct at a confrontation angle effective for cannulating the duct as it is grasped between the jaws of the grasping forceps component.

23 Claims, 5 Drawing Sheets

ENDOSCOPIC CHOLANGIOGRAM GUIDE INSTRUMENT AND METHOD OF USE

BACKGROUND OF THE INVENTION

The present invention is directed to a method for cannulating a biliary duct as part of a laparoscopic cholangiographic surgical procedure, and to a guide instrument therefor for presenting a catheter or the like to the biliary duct at a select confrontation angle.

Cholecystectomy or gallbladder removal has been carried out in a structured surgical manner since about 1882. The heretofore conventional approach to the procedure has involved the surgical opening of the body cavity, typically via a right quadrant incision, and direct hand access to the organ on the part of the surgeon aided by three-dimensional vision and touch. This surgical procedure continued for over 100 years until the 1980s when a new treatment employing laparoscopy somewhat abruptly supplanted the earlier orthodox procedure. The appeal of this new treatment modality resides in the less invasive character of the procedure, which is carried out with correspondingly less pain, incision, and scar, shorter term hospitalization, and improved cost considerations.

In general, the laparoscopic approach to cholecystectomy commences with the insufflation of the peritoneal cavity of the anesthetized patient. Typically, this expansion of the cavity (pneumoperitoneum) is carried out by the controlled insertion of an insufflating agent such as carbon dioxide through a supraumbilically inserted Verres needle. That needle is operatively associated with an insufflator machine, usually providing a pressure and flow rate control over the insufflating agent. A sequence of cannulas are placed into the peritoneal cavity using sharp, removable inserts called trocars. These cannulas are valved devices through which a video imaging camera and light source along with various thin, elongate instruments can be passed and manipulated from outside of the patient's body during the procedure. Cannulas vary in port diameter, ranging, for instance, from 5 mm to 18 mm. Generally, the first cannula is installed adjacent the umbilicus and serves to initially receive a laparoscope or video camera and light source. It is the video output of this device as observed by the surgeon at a video monitor which provides all of the visual perceptive data for hand maneuvering the elongate laparoscopic instruments. As the video camera is guided by a surgical assistant, these instruments, having a necessary length of about 18 inches (45.72 cm), are held at one end by the surgeon who, while viewing the video monitor, carries out refined and delicate dissecting, isolating and clamping maneuvers within the moving, dynamic environment of the peritoneal cavity.

The gallbladder is the reservoir for bile which, with the hepatic, cystic, and common bile ducts, forms the excretory apparatus of the liver. Conical or pear shaped in gross anatomy, the gallbladder exists as a musculo-membranous sac lodged in a fossa on the undersurface of the right lobe of the liver, and extends from near the right extremity of the transverse fissure to the anterior border of the organ. It is about 4 inches (10.16 cm) in length, 1 inch (2.54 cm) in breadth at its widest part, and holds from eight to ten drachms. The organ is divided into a fundus, body, and neck or infundibulum. The fundus or broad extremity is directed downward, forward and to the right, and projects beyond the anterior border of the liver. The body and neck are directed upward and backward to the left. The vascular system of the gallbladder is derived from branches of the hepatic artery.

The upper surface of the gallbladder is attached to the liver by connective, i.e., areolar, tissue and vessels. The under surface is covered by peritoneum, which is reflected on to it from the surface of the liver. Occasionally, the whole of the organ is invested by the serosa membrane, and is then connected to the liver by a kind of mesentery. Adipose tissue often invests the gallbladder and its biliary and vascular anatomy.

In wall structure, the gallbladder consists of three coats, namely, serous, fibrous and muscular, and mucous. The external or serous coat is derived from the peritoneum and completely invests the fundus, but covers the body and neck only on their under surface. The fibro-muscular coat is a thin but strong layer which forms the framework of the sac and consists of dense, fibrous tissue which interlaces in all directions. The internal or mucous coat is loosely connected with the fibrous layer and is covered with columnar epithelium. The mucous membrane secretes an abundance of thick, viscid mucus.

As aforementioned, both the gallbladder and liver are associated with a biliary anatomy including three biliary ducts: the cystic duct, the common bile-duct (ductus communis choledochus), and the hepatic duct. The cystic duct, typically exhibiting a very small diameter of about ⅛ inch (3.175 mm) joins the hepatic duct to form a common bile duct which extends to an orifice upon the summit of the papilla situated at the inner side of the descending portion of the duodenum. The external coat of the cystic duct is fibrous and composed of strong fibro-areolar tissue with a certain amount of muscular tissue arranged in a circular manner around the duct.

As gall stones may be present in the common bile duct, under earlier, open surgical cholecystectomy procedures, the surgeon has been able to palpate the common bile duct and visualize its diameter for determining whether a cholangiogram would be necessary to detect any occult stones. This procedure was essentially straightforward utilizing the surgeon's stereoscopic direct vision and tactile senses at the fingertips. However, in laparoscopic surgery, the common bile duct is not tactilely accessible by the surgeon, but is viewed two-dimensionally and remotely on a television monitor, making it difficult for the surgeon to appreciate turns in the ductal structures. Thus, and as retained stones in the biliary anatomy present the possibility for injuries to the major ductal structures during laparoscopic cholecystectomy, a cholecystcholangiographic protocol is generally indicated for management of ductal stones. Indeed, cholangiography is useful both for demonstrating the cystic duct/common hepatic duct junction to delineate abnormal anatomy, and for indicating the presence of any stones in the common bile duct.

One technique for cholecystcholangiography involves retracting the gallbladder laterally and elevating it up to the abdominal wall. Upon being brought into apposition with the abdominal wall, the gallbladder is then punctured percutaneously with a needle to aspirate bile and to effect a decompression. A syringe of contrast material such as a barium fluid or the like then is attached to the needle for refilling the gallbladder with an amount of the contrast material equal in volume to the amount of bile which was aspirated. At this point, the gallbladder is viewed radiographically with a fluoroscope or the like to assess the biliary anatomy and to determine whether stones are present within the common bile duct.

Although the above-described cholangiographic technique is relatively easily effected given the constraints of two-dimensional remote vision and diminished tactile data, the injection of contrast fluid directly into the sac of the gallbladder sac engenders a risk of flushing any stones contained therein into the ductal system where removal is made more difficult. Accordingly, a cystic duct cholangiography protocol is often specified. In this protocol, the gallbladder is grasped with atraumatic grasping forceps at the fundus and, optionally, at the infundibulum to place the cystic duct in tension. Any adhesions between the gallbladder and the adjacent organs, e.g., omentum, right colon flexure and duodenum, may be bluntly divided or transected with a hooked electrode or scissors. With the gallbladder separated and adequate traction maintained, the cystic duct is dissected from its areolar and/or adipose investment using forceps, hook electrodes, or scissors. In this regard, it is generally preferred that dissection is begun at the infundibulum and proceeds in the direction of the common bile duct to expose junction of the cystic and hepatic ducts.

Upon adequate exposure of the duct, the upper neck of the gallbladder is then closed by peripherally clipping the cystic duct near its junction with the infundibulum of the gallbladder. With the gallbladder grasped near the infundibulum to stretch the cystic duct, an instrument such as a pair of laparoscopic microscissors is used to partially transect the cystic duct on the common bile duct side of the previously placed clip. Following the partial transection of the cystic duct, a cholangiography catheter is percutaneously inserted at an angle to orient the catheter towards the opening in the duct. The catheter is selected as being flexible and having outer diameter suited for insertion into the duct. The tip of the catheter is guided into the cystic duct through the opening, and is secured in the duct by clipping. It generally is preferred that saline is injected through the catheter during clipping to assure its potency. Once the catheter is secured within the cystic duct, cholangiography is performed in a routine fashion.

After satisfactory cholangiograms have been obtained, the cholecystectomy procedure continues with the retrieval of any ductal stones and, thereafter, with the division of the cystic duct. With respect to the division of the cystic duct, the duct first is clipped centrally near its junction with the common bile duct. The duct then is divided between the central clip and the peripheral clip previously placed near the infundibulum of the gallbladder. As the duct is divided, traction is maintained on the neck of the gallbladder away from the liver to more clearly expose the cystic artery.

With the cystic duct divided, the cystic artery next may be addressed. Indeed, it is preferred to first divide the cystic duct before the cystic artery is dissected as closure and division of the cystic duct as a first step permits a better identification and a safer closure of the cystic artery. As with the cystic duct, the cystic artery, for its identification, also may have to be dissected free of an areolar and/or adipose investment, again with the use of forceps, hook electrodes, or scissors. Division of the artery then may proceed via a double clip ligation and a transection with scissors between the clips.

Following the division of the cystic duct and arteries, the intraoperative procedure continues with the dissection of the gallbladder from the liver. Generally, this dissection proceeds by alternately retracting the gallbladder medially and laterally with concurrent elevation to place the interposing tissue under tension. With the interposing tissue placed in tension, it may be separated either bluntly with dissecting forceps, sharply with scissors, or with a monopolar electrosurgical instrument or a bipolar forceps. The gallbladder then may be removed from the body through a lateral trocar.

For further information concerning laparoscopy and its use in conjunction with cholecystectomy, reference is made to the following publications, the disclosures of which are expressly incorporated herein by reference:

Saleh, J. W., "Laparoscopy," W. D. Saunders Co., 1988.

Graber, J. N., Schultz, L. S., Pietrafitta, J. J., and Hickok, D. F., "Laparoscopic Abdominal Surgery," McGraw-Hill, Inc., 1993.

Hunter, J. G., and Sackier, J. M., "Minimally Invasive Surgery," McGraw-Hill, Inc., 1993.

Cuschieri, A., Buess, G., and Périssat, J., "Operative Manual of Endoscopic Surgery," Springer-Verlag, 1992.

As aforementioned, a cholangiogram protocol generally is indicated in laparoscopic cholecystectomy procedures to assist both in the detection of bile duct stones and in the visualization of ductal abnormalities and the like. Indeed, the above-described cystic duct cholangiography protocol often is specified in cholecystcholangiography to minimize the risk of stone migration from the gallbladder sac into the ductal system. However, there has been reported a 23.3% failure rate, defined as the inability to cannulate or inject the cystic duct, for attempted laparoscopic cholangiography. "The Southern Surgeons Club: A Prospective Analysis of 1518 Laparoscopic Cholecystectomies," New England Journal of Medicine, 324:1073–1078, 1991. Kumar has observed that this relatively high failure rate for attempted laparoscopic cholangiography provides one explanation for the sporadic use of cholangiograms in laparoscopic cholecystectomies despite the demonstrated advantages thereof. Kumar, S. S., "Laparoscopic Cholangiography: A New Method and Device," Journal of Laparoendoscopic Surgery, 2(5):247–254, 1992.

Kumar additionally has observed that reasons for the high failure rate may be attributed to the narrow, tortuous structure of the cystic duct anatomy which can defy cannulation, and to the fact that the cannulating devices heretofore known in the art may confront a difficult cannulation angle which complicates the insertion of the catheter into the duct. Although such devices, as described in Smith III, U.S. Pat. No. 4,817,604, Lazarus et al., U.S. Pat. No. 4,792,339, Uddo, Jr., U.S. Pat. No. 4,735,615, and Berlin et al., U.S. Pat. No. 4,484,911, for open surgery cholangiography, and in Noda, U.S. Pat. No. 5,071,412, for laparoscopic cholangiography, have been proposed to facilitate cholangiographic procedures, the failure rate for intraoperative cystic duct cholangiograms, and especially for laparoscopic cholangiograms, nevertheless has remained unacceptable. Because of the continuing difficulties encountered in performing cystic duct laparoscopic cholangiography, Kumar has proposed an alternative method wherein the infundibulum, i.e., ampulla or Hartmann's pouch, is cannulated instead of the cystic duct. Such method, as is described in Kumar, U.S. Pat. No. 5,224,931, entails the use of a clamp having a 5 mm grasper with atraumatic jaws and a side channel for introduction of a cholangiocatheter formed as having a 22-gauge needle terminating one end of a clear, polymeric catheter. After completion of routine peritoneoscopy and cephalad retraction of the gallbladder fundus by a grasper inserted through the right lateral subcoastal port, the clamp is introduced into the peritoneal cavity through the right mid-subcoastal port. The clamp then is applied across the lower part of the body of the gallbladder just above the infundibulum. The jaws of the clamp are provided to extend across the gallbladder for its division into two separate sections, namely, an anterior compartment and a posterior or medial compartment which includes mainly the bulging pouch of the infundibulum. The infundibulum is punctured at a 15° angle with the needle of the catheter which has been inserted through the side channel of the clamp. Approximately 5 to 15 ml of dye then is injected through the catheter under C-arm fluoroscopy or the like. Upon completion of the cholangiography, the catheter is removed, and the proximal port of the side channel is occluded with a rubber cap to avoid loss of the pneumoperitoneum. The clamp then may be used as a regular grasper for the completion of the operation.

Although success rates of over 80% have been reported with the Kumar clamp, commentators have noted several disadvantages with the clamp and its method of use. Principally, these disadvantages stem from a perception that the clamp and its methodology are inapplicable when the gallbladder exhibits a cholecystitis pathology, and that the cholangiogram obtained is less desirable than a true cystic duct cholangiogram. "New Laparoscopic Clamp Eases Intraoperative Cholangiography," General Surgery & Laparoscopy News, pp. 1–19, September (1993). Accordingly, there has existed and remains a need for laparoscopic instruments and techniques which facilitate the obtaining of the cystic duct cholangiograms which are considered preferred. It is apparent that such instruments and techniques would be well-received by practitioners and would represent an important improvement in laparoscopic surgery.

BROAD STATEMENT OF THE INVENTION

The present invention is addressed to a guide instrument for cannulating a biliary duct with a flexible catheter, and to a method of using the same as part of a laparoscopic cholangiographic surgical procedure. In having a guide tube which is rotatable about the longitudinal axis of the shaft of a grasping forceps component, the guide instrument of the present invention provides for a confrontation radius facilitating the presentation of a catheter expressed through an internal channel of the guide tube to a biliary duct at a confrontation angle effective for cannulating the duct as it is grasped with the grasping forceps component. The instrument thereby assists the laparoscopic catheterization of the cystic duct or the like in allowing the surgeon to select a confrontation angle between the catheter and the duct which is the most effective for cannulation. Moreover, the instrument generally speeds the catheterization procedure in maintaining the proper alignment between the grasping forceps component of the instrument and the catheter being expressed from the guide tube. Advantageously, the instrument may be configured to be received within a standard 5 or 10 mm cannula port, and may be provided to effect a hermetic sealing of the port to prevent any loss of the pnenumopertoneium as the catheter is inserted through the guide tube. As will be apparent, the instrument of the present invention is especially suited for use in a laparoscopic cholecystcholangiography surgical method in the obtaining of a cystic duct cholangiogram prior to the transection of the duct.

It is therefore a feature of the invention to provide a guide instrument for cannulating a biliary duct with a flexible catheter as part of a laparoscopic cholangiographic surgical procedure. The guide instrument has a grasping forceps component formed of an elongate shaft extending along a longitudinal axis between a first and a second end. A pair of jaws are positioned at the first end of the shaft and are mutually pivotally coupled thereat for movement between an opened and a closed orientation for selectively grasping the duct. An actuator positioned at the second end of the shaft is coupled in a drive relationship with the jaws for moving the jaws between the opened and closed orientations. An elongate, generally cylindrical guide tube is slidably supported along the longitudinal axis of the elongate shaft and is formed as having an internal catheter channel therethrough. The catheter channel has a central axis which is spaced radially from the longitudinal axis, and is provided to extend between an input end for receiving the catheter and an output end for expressing the catheter from the guide tube. The guide tube is rotatable about the longitudinal axis to define with the central axis of the catheter channel a first confrontation radius for presenting the catheter expressed from the output end of the catheter channel to the biliary duct at a confrontation angle effective for cannulating the duct as it is grasped between the jaws of the gasping forceps component.

It is a further feature of the present invention to provide a method for cannulating a biliary duct with a flexible catheter as part of a laparoscopic cholangiographic surgical procedure. A guide instrument is provided which comprises a grasping forceps component and a guide tube which is slidably supported on the grasping forceps component and has an internal catheter channel therethrough which extends between an input end for receiving the catheter and an output end for expressing the catheter from the guide tube. The guide tube is rotatable about the grasping forceps component to define a confrontation radius for presenting the catheter expressed from the output end of the catheter channel to the biliary duct at a confrontation angle effective for cannulating the duct. The duct is grasped with the grasping forceps component, and the catheter is directed through the catheter channel of the guide tube to express the catheter from the output end thereof. The guide tube is rotated about the grasping forceps component to present the catheter expressed from the output end of the guide tube to the biliary duct at a confrontation angle effective for cannulating the duct. Lastly, the catheter is inserted into the duct for its cannulation.

It is yet a further feature of the invention to provide a guide instrument for presenting a second instrument to a biliary duct as part of a laparoscopic cholangiographic surgical procedure. The guide instrument has a grasping forceps component formed of an elongate shaft extending along a longitudinal axis between a first and a second end. A pair of jaws are positioned at the first end of the shaft and are mutually pivotally coupled thereat for movement between an opened and a closed orientation for selectively grasping the duct. An actuator positioned at the second end of the shaft is coupled in a drive relationship with the jaws for moving the jaws between the opened and closed orientations. An elongate, generally cylindrical guide tube is slidably supported along the longitudinal axis of the elongate shaft and is formed as having an internal instrument channel therethrough. The instrument channel has a central axis which is spaced radially from the longitudinal axis, and is provided to extend between an input end for receiving the catheter and an output end for expressing the catheter from the guide tube. The guide tube is rotatable about the longitudinal axis to define with the central axis of the instrument channel a first confrontation radius for presenting the second instrument expressed from the output end of the instrument channel to the biliary duct at a select confrontation angle as the duct is grasped between the jaws of the grasping forceps component.

The invention, accordingly, comprises the apparatus and method possessing the construction, combination of elements, and arrangement of parts and steps which are exemplified in the following detailed description. Reference to that description and to the accompanying drawings should be had for a fuller understanding and appreciation of the nature and objects of the invention, although other objects may be obvious to those skilled in the art.

BRIEF DESCRIPTION OF THE DRAWINGS

For a fuller understanding of the nature and objects of the invention, reference should be had to the following detailed description taken in connection with the accompanying drawings wherein.

The drawings will be described further in connection with the following Detailed Description of the Invention.

DETAILED DESCRIPTION OF THE INVENTION

The precepts of the endoscopic guide instrument which is the subject of the present invention are described hereinafter in connection with its utilization in a laparoscopic cholecystcholangiography surgical protocol. However, it will be appreciated that the subject instrument may find utility in other laparoscopic surgical protocols procedures which involve the grasping and alignment of ductal tissues and the like. Thus, the disclosure to follow should be construed as illustrative rather than in a limiting sense.

Figures 1, 1A, 2, 3:
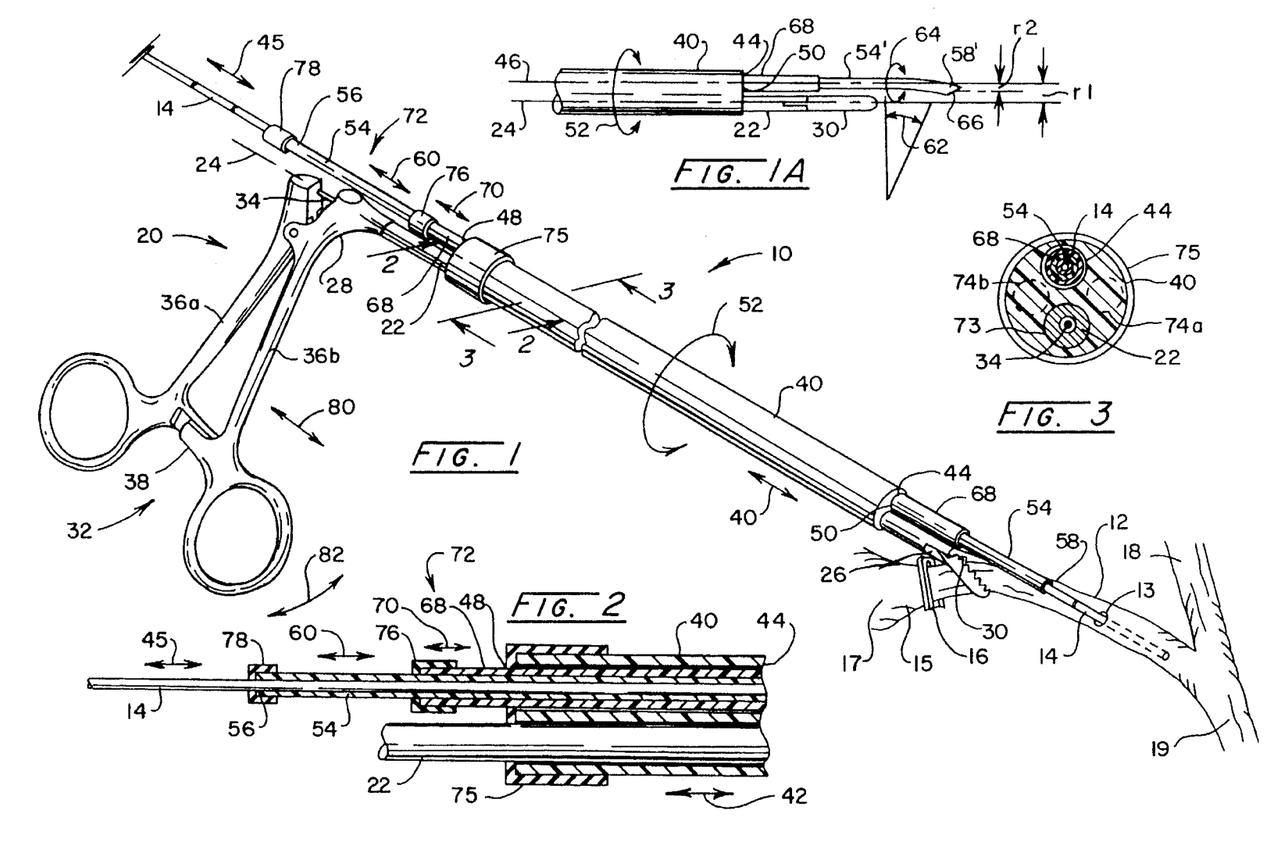
FIG. 1 shows a perspective view of a guide instrument in accordance with the present invention for presenting a catheter or the like to a biliary duct at a select confrontation angle as part of a laparoscopic cholangiographic surgical procedure.
FIG. 1A is a fragmentary, enlarged side elevational view of the output end of the guide instrument of FIG. 1 showing the catheter cannula thereof as being formed as having an acutely angled output end which describes a generally arcuate locus as the catheter cannula is rotated.
FIG. 2 is a cross-sectional view of the guide instrument of FIG. 1 taken through line 2—2 of FIG. 1.
FIG. 3 is a cross-sectional view of the guide instrument of FIG. 1 taken through line 3—3 of FIG. 1.
Figure 4:
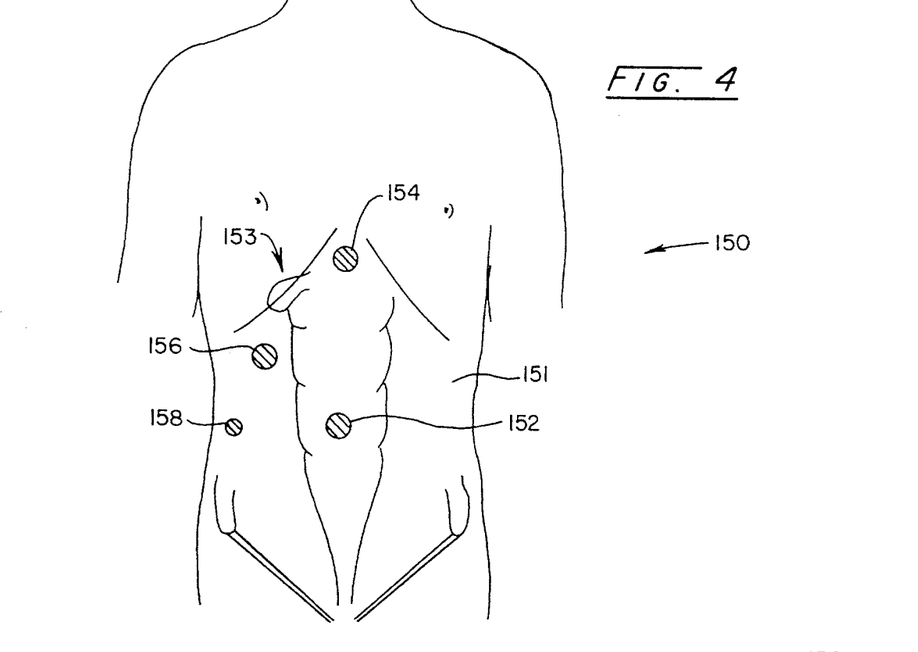
FIG. 4 is a ventral plan view of the abdomen of an insufflated patient showing the location of the cannula ports for a laparoscopic cholecystcholangiography surgical protocol.

Referring to the figures and looking in particular to FIG. 1, an embodiment of the endoscopic guide instrument of the subject invention is represented generally at 10 in conjunction with its use in cannulating a biliary duct, 12, with a flexible catheter, 14, as part of a laparoscopic cholangiographic surgical procedure. Biliary duct 12 is shown as having been partially-transected to form an opening, 13, into which catheter 14 is inserted. For illustrative purposes, biliary duct 12 is represented as a cystic duct which extends from the infundibulum, 15, which is shown clipped with a staple 16, of a gall bladder, 17, to a junction with a hepatic duct, 18, forming a common bile duct, 19.

In general construction, instrument 10 comprises a grasping forceps component, shown at 20, and an elongate, generally cylindrical guide tube, 40. Grasping forceps 20 is provided as being formed of an elongate shaft, 22, extending along a longitudinal axis, 24, between a first end, 26, and a second end, 28. A pair of jaws, 30, are positioned at first end 26 and are mutually pivotally coupled thereat for movement between an opened and a closed orientation for selectively grasping duct 12. An actuator, shown at 32, is positioned at second end 28 of shaft 22 and is coupled in a drive relationship via a drive member, 34, with jaws 30 for their movement between the opened and closed orientations. Preferably, actuator 32 is provided as a manually-actuable, scissors-type arrangement which includes a pair of looped handles, 36a and 36b, which are coupled to drive member 34 for actuating drive member 34 to move jaws 30 between their opened and closed orientations. As is shown at 38, handles 36 may be configured to effect a mechanical, interlocking engagement therebetween to lock jaws 30 in their closed orientation. Alternatively, a trigger-type assembly (not shown) may be substituted for actuator 32. Commercially-available biliary duct or endoscopic forceps of the type described in connection with grasping forceps 20 are shown in Hunter and Sackier, pp. 157–158, and in Graber and Schultz, pp. 23–24.

As is shown at 42, guide tube 40 of instrument 10 is slidably supported along the longitudinal axis 24 of shaft 22, and is formed as having an internal catheter channel, 44, extending therethrough which is configured to receive catheter 14 as, as is shown at 45, it is slidably directed through guide tube 40. As may be seen through additional reference to FIG. 1A, catheter channel 44 has a central axis, 46, which is spaced radially from longitudinal axis 24 of shaft 22, and is provided to extend between an input end, 48, for receiving catheter 14 and an output end, 50, for expressing catheter from guide tube 40. As is shown at 52 of FIG. 1, guide tube 40 is made rotatable about longitudinal axis 24 to define with central axis 46 of catheter channel 44 a first confrontation radius, $r_1$ (FIG. 1A), for presenting the catheter 14 expressed from the output end 50 of catheter channel 44 to biliary duct 12 at a select confrontation angle effective for cannulating duct 12 as it is grasped between jaws 30 of grasping forceps 20.

For illustrative purposes, channel 44 of guide tube 40 has been shown as a catheter channel which slidably receives catheter 14. However, channel 44 advantageously may be provided as an instrument channel having an internal diametric extent or lumen configured to receive a variety of laparoscopic surgical instrument such as cholangioscopes, microscissors, blunt dissectors, mono or bipolar electrosurgical scalpels, surgical staplers and clip applicators, French catheters, and grasping or other forceps. Thus, it will be appreciated that in its broadest sense, the present invention involves a guide instrument for presenting a second instrument to a biliary duct or the like at a select confrontation angle as part of a laparoscopic surgical protocol such as a cholecystcholangiographic procedure.

It will be appreciated that in providing for the rotation of guide tube 40 about longitudinal axis 24 to define confrontation radius $r_1$, guide instrument 10 of the present invention facilitates the endoscopic cannulation of ductal structures such as biliary duct 14 by allowing the surgeon to select a confrontation angle between the catheter and the duct which is the most effective for the insertion of the catheter into the duct. Thus, by increasing the stable cannulation opportunities for the surgeon and by maintaining a proper alignment between grasping forceps 20 of the instrument and the catheter 14 being expressed from guide tube 40, instrument 10 both speeds the catheterization of the duct and allows for the catheterization of ducts exhibiting anatomies which heretofore would have defied cannulation. Such speed and flexibility are occasioned notwithstanding the constraints of two-dimensional remote vision and diminished tactile response which unavoidably attended any laparoscopic surgical procedure.

Continuing with FIG. 1, guide instrument 10 is shown as further comprising an elongate catheter cannula, 54, which is slidably received within catheter channel 44. Catheter cannula 54 is configured as having an internal diametric extent or lumen configured to slidably receive catheter 14 therethrough, and is provided to extending between an input end, 56, for supporting the catheter 14 received at the input end 48 of catheter channel 44, and an output end, 58, for supporting the catheter expressed from the output end 50 of catheter channel 44. Advantageously, and as is shown at 60, catheter cannula 54 is extensible from the output end 50 of catheter channel 44 for supporting the catheter 14 as it is presented to biliary duct 12. Cannula 54 may be extended to and even may be inserted into opening 13 of duct 12 to assist in the insertion of catheter 14 thereinto.

Looking additionally to FIG. 1A, catheter cannula 54 is shown at 54' as having an output end 58' which, as is shown at 62, is acutely angled with respect to central axis 46 of channel 44 to describe a generally arcuate locus when, as is shown at 64, cannula 54' is rotated about central axis 46 within catheter channel 44. Preferably, angle 62 is selected as being about 4° such that the arcuate locus defines a second confrontation radius, $r_2$, about central axis 46 for presenting the catheter 14 expressed from the output end 50 of catheter channel 44 to biliary duct 12 at a confrontation angle effective for cannulating the duct. The laparoscopic surgeon, therefore, by the rotational and/or translational actuation of guide tube 40 and cannula 54 or 54', may advantageously affect the positioning relative to duct 12 of catheter 14 for its facile insertion thereinto. Further in this regard, output end 58' of cannula 54' may be provided with a tip, 66, which is angled at about 45° to about 60° relative to central axis 46 to provide a generally elliptical or needle-shaped opening which both facilitates the insertion of output end 58' into opening 13 of duct 12 (FIG. 1), and maintains the generally angular orientation of catheter 14 as it is expressed from cannula 54'.

Returning to FIG. 1, instrument 10 additionally may be provided with a guide sleeve, 68, having an outer diametric extent configured to be received by catheter channel 44 and an inner diametric extent configured to receive catheter cannula 54. Where instrument 10 is used as a guide instrument for presenting a second instrument to a biliary duct or the like, guide sleeve 68 may be configured, depending upon the relative diameter of the second instrument, to receive the second instrument, or, alternatively, it may be removed completely with the second instrument being received directly within channel 44. Through the provision of guide sleeve 68, the flexibility of instrument 10 is thereby enhanced in that such guide sleeves may be employed to specifically size channel 44 for its receipt of catheters and instruments of various outer diameters.

As is shown at 70, guide sleeve 68 also may be provided to be extensible from the output end 50 of catheter channel 44. Thus, and as may be appreciated best through additional reference to FIG. 2, a telescopic assemblage, shown generally at 72, of guide tube 40, guide sleeve 68, catheter cannula 54, and catheter 14 may be envisaged. That is, guide tube 40 is slidably translatable along shaft 22, and guide sleeve 68, catheter cannula 54, and catheter 14 are each slidably extendible from guide tube 40 to variably increase or decrease the reach of instrument 10 within the peritoneal cavity of the patient. For cholangiographic applications, the linear translation of telescopic assembly 72 provides an additional degree of freedom which the surgeon may employ to present catheter 14 to biliary duct 12 at an effective confrontation angle.

Looking additionally to FIG. 3, the concentrically cylindrical arrangement of telescopic assembly 72 (FIG. 2) is shown in enhanced detail. For housing such an arrangement, it is preferred that guide tube 40 is provided as a rod or other extrusion which is machined or otherwise formed to include an internal catheter cannula 44. In like manner, tube 40 additionally may be formed as having an internal support channel, 73, extending therethrough for receiving shaft 22 and thereby slidably rotatably supporting guide tube 40 on shaft 22. Guide tube 40 also may formed has having a number of auxiliary channels, two of which are shown at 74a and 74b, each of which extends between an input end and an output end. Advantageous, auxiliary channels 74 each may be configured as having an inner diametric extent configured to slidably receive a variety of laparoscopic surgical instruments for enhancing the utility and flexibility of instrument 10.

The generally cylindrical configuration of telescopic assembly 72 also facilitates its receipt within a standard 5 or 10 mm cannula port, and may be provided to effect a hermetic sealing of the port to prevent any loss of the pnenumopertoneium as the catheter is inserted through the guide tube. In this regard, as may best be seen with reference to FIGS. 1 and 2, a series of end caps, 75, 76, and 78, which preferably are formed of an elastomeric material such as a rubber, a polytetrafluoroethylene, a polyethylene, or the like, may be interposed between guide tube 40, guide sleeve 68, catheter cannula 54, and catheter 14 to seal instrument 10. In the arrangement shown, end cap 75 is disposed about the input end 48 of guide tube 40, and is configured to receive guide sleeve 68 and elongate shaft 22 of grasping forceps 20 therethrough. In like manner, end cap 76 is disposed about guide sleeve 68 and is configured to receive catheter cannula 54 therethrough, and end cap 78 is disposed about the output end 56 of catheter cannula 54 and is configured to receive catheter 14 therethrough.

When used, for example, in the laparoscopic cholangiography procedure depicted in FIG. 1, instrument 10 desirably provides the surgeon with a number of degrees of freedom for movement within the operative field. That is, in addition to the translation and axial rotation movements represent by the arrows 42, 45, 52, 60, 64, 70 described hereinbefore, additional degrees of freedom also are provided as is represented at 80 and 82. Accordingly, the laparoscopic surgeon is provided with the ability to position instrument 10 along any of a number of planes for maintaining a proper alignment between the grasping forceps 20 of the instrument and the catheter 14 being expressed from guide tube 40, and for presenting the catheter 14 to the biliary duct at an effective confrontation angle.

As to the construction of instrument 10, and specifically of guide tube 40, guide sleeve 68, and catheter cannula 54, it is preferred that such components be formed of an extruded or pultruded polymeric material such as a class 6 polyvinylchloride or an equivalent which is approved for in vivo applications. For use with a standard grasping forceps 20 having a length of about 14 inches (35.6 cm) and a shaft diameter of about 0.2 inch (5 mm), guide tube 40 may be configured as having an overall length of about 8 inches (21 cm), a 0.146 inch (3.71 mm) diameter catheter channel 44, a 0.20 inch (5.08 mm) support channel 73, and a 0.404 inch (10.26 mm) outer diameter if insertion though a 10 mm cannula port is contemplated. Alternatively, guide tube 40 may be configured has having a 0.197 inch (5 mm) outer diameter if insertion through a 5 mm port is desired. Similarly, guide sleeve 68 may be configured as having a length of 10 inches (25.4 cm), an inner diameter of 0.126 inch (3.2 mm), and an outer diameter of 0.146 inch (3.71 mm), for receiving a catheter cannula 54 configured as having a length of 12.5 inch (31.7 cm), an outer diameter of 0.126 inch (3.2 mm), and an inner diameter of 0.066 inch (1.68 mm) for receiving a standard cholangiography catheter. It will be appreciated that the relative sizes of guide tube 40, guide sleeve 68, and catheter cannula 54 may be varied depending on design considerations and the intended use contemplated for instrument 10.

Referring next to the sequence of FIGS. 4–11, the methodology of the present invention is illustrated in connection with the utilization of guide instrument 10 in a laparoscopic cholecystcholangiography surgical protocol. Looking initially to FIG. 4, a ventral view of an insufflated patient is shown generally at 150 wherein the patient is positioned for intra-abdominal access to the peritoneal cavity, 151. A number of representative cannula ports are depicted, including an umbilical port, 152, an epigastric port, 154, a mid-clavicular port, 156, and an anterior auxiliary port, 158. Umbilical port 152, epigastric port 154, and mid-clavicular port 156 may be provided as having 10 mm port diameters, while anterior auxiliary port 158 may be provided as having a 5 mm port diameter. However, the number, port diameter size, and even the location of the cannula ports used to access the gall bladder and the biliary anatomy thereof, which are broadly represented at 153, may vary depending on such factors as the body habitus of the patient and the internal anatomical structure of the patient.

Figure 5:
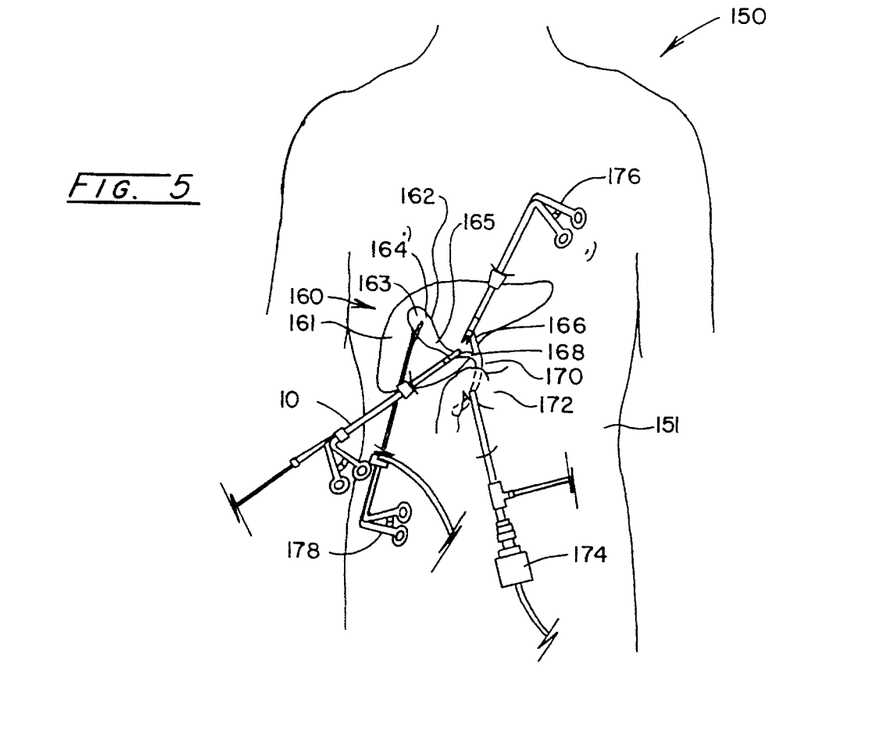
FIG. 5 is a ventral plan view of the patient of FIG. 5 showing the internal biliary anatomy of the peritoneal cavity including the gallbladder and cystic duct, and also showing the cannula ports as holding an arrangement of laparoscopic instruments including the guide instrument of FIG. 1.

Turning next to FIG. 5, cavity 151 is shown as having inserted thereinto a number of representative laparoscopic surgical instruments passed through ports 152, 154, 156, and 158 (FIG. 4), and into visual or tactile contact with the internal biliary anatomy, represented schematically at 160, of patient 150. In this regard, biliary anatomy 160 may be seen to include a liver, 161, and an attached gallbladder, 162, which may be divided in structure into an upper fundus, 163, an intermediate body, 164, and a lower infundibulum, 165. Gallbladder 162 has an associated ductal system comprised of a hepatic duct, 166, and a cystic duct, 168, leading from, respectively, liver 161 and gallbladder 162, and junctioning to form a common bile duct, 170, leading into a duodenum, 172. Gallbladder 162 also has an associated vascular system, of which a cystic artery, 173 (FIG. 6), is shown. As is commonly practiced, although, again, the exact arrangement may vary, ports 152, 154, and 158 receive, respectively, a laparoscope or video camera, 174, a pair of microscissors, 176, and a grasping-type forceps, 178. In accordance with the present invention, mid-clavicular port 156 receives guide instrument 10 of FIG. 1.

Figure 6:
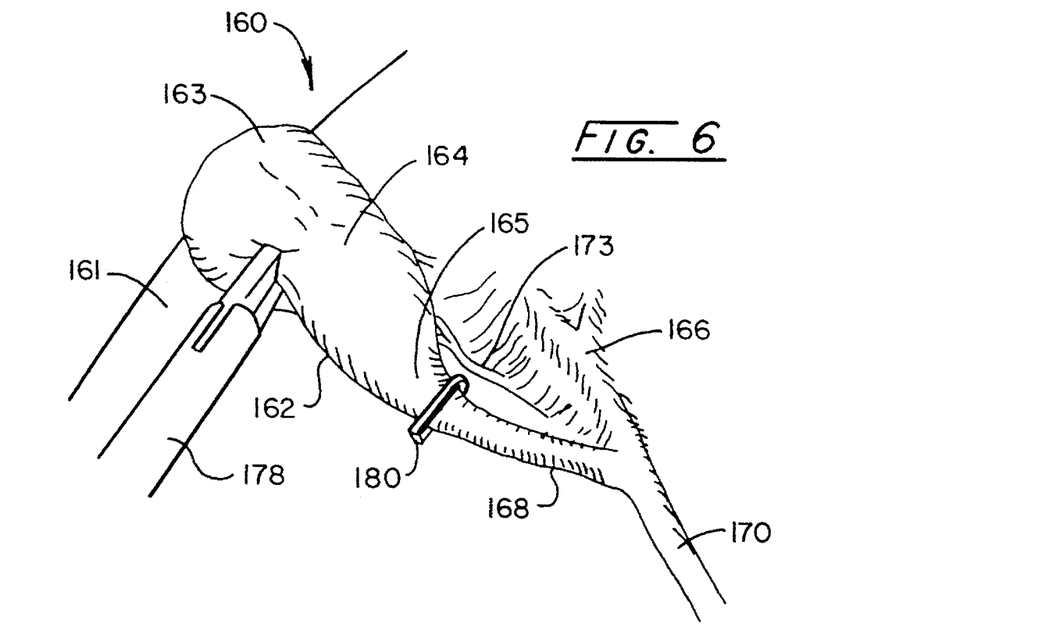
FIG. 6 is an enlarged perspective view portraying the internal view of a laparoscopic cholecystcholangiography surgical procedure wherein the gallbladder is intra-abdominally retracted to place the cystic duct in tension.

Proceeding to FIG. 6, wherein biliary anatomy 160 is shown in enhanced detail with gallbladder 162 having been excised from any adhesions and dissected from its investment tissue, the laparoscopic cholecystcholangiography procedure utilizing instrument 10 of the present invention commences with the grasping with grasping forceps 178 of the fundus 163 of gallbladder 164, and the medial retraction thereof to place cystic duct 168 in tension. Optionally, infundibulum 165 of gallbladder 162 additionally may be grasped and mobilized with a second pair of grasping forceps (not shown). The lower portion or neck of infundibulum 165 is shown as having been clipped with a surgical clip, 180, or the like prepatory to the delivering of a contrast fluid into cystic duct 168.

Figure 7:
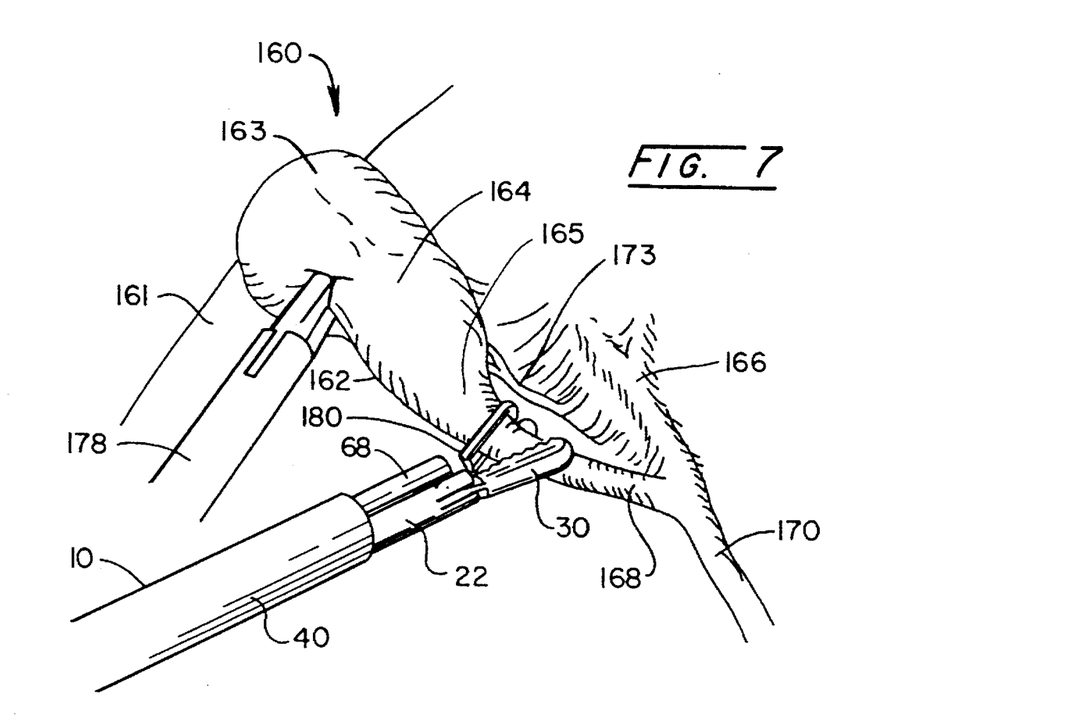
FIG. 7 is an enlarged perspective view of the continuing laparoscopic surgical procedure of FIG. 6 showing the grasping of the cystic duct with the guide instrument of FIG. 1.
Figure 8:
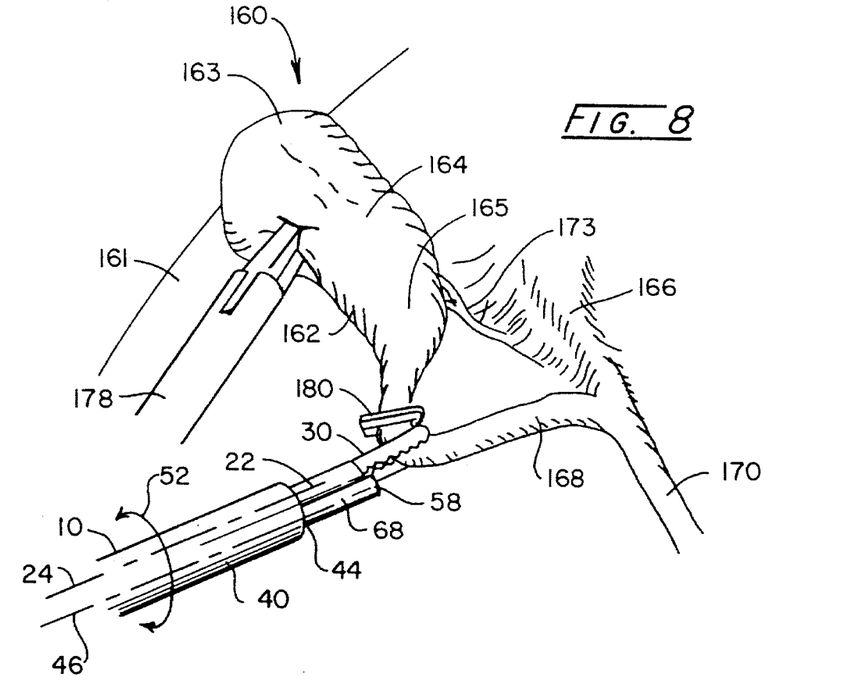
FIG. 8 is an enlarged perspective view of the continuing laparoscopic surgical procedure of FIG. 6 showing the rotation of the guide tube of the guide instrument of FIG. 1 for presenting catheter expressed from the output end thereof to the cystic duct at a confrontation angle effective for cannulating the duct.

Continuing with FIG. 7, with traction maintained on gallbladder 162, instrument 10 is introduced through the mid-clavicular port 156, and is moved into presentation with cystic duct 168. For mobilizing cystic duct 168 prior to its partial transection, the duct is grasped between jaws 30 of instrument 10. As is shown in FIG. 8, with duct 168 secured within jaws 30, instrument 10 may be manipulated through the degrees of freedom shown in FIGS. 1, 1A, and 2 to retract duct 168 and to effect its general alignment with longitudinal axis 24 of shaft 22. In this regard, as is shown at 52, guide tube 40 may be rotated about longitudinal axis 24 to orient the central axis 46 of catheter channel 44 at a confrontation angle effective for cannulating duct 168.

Figure 9:
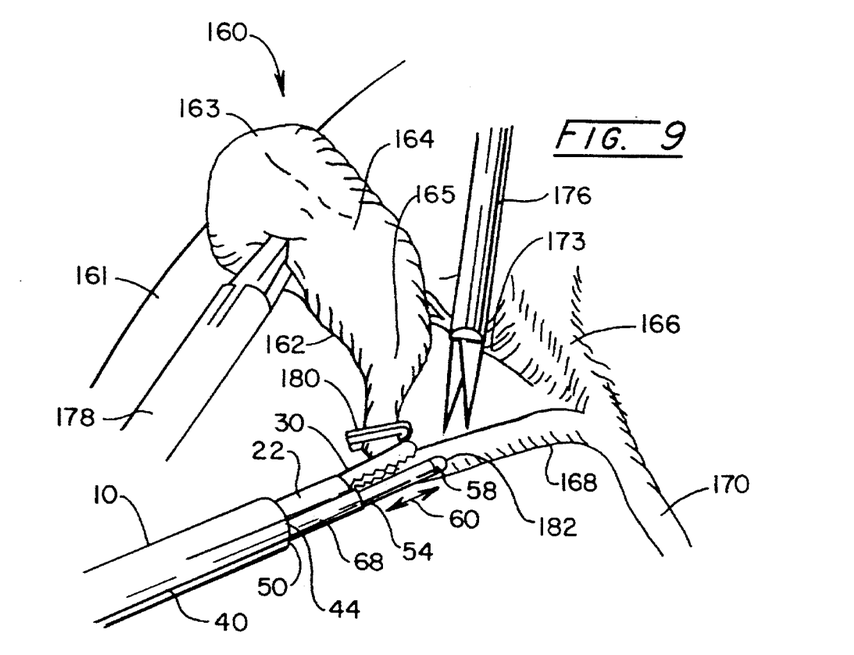
FIG. 9 is an enlarged perspective view of the continuing laparoscopic surgical procedure of FIG. 6 showing the extension of a catheter cannula to the cystic duct for supporting the catheter as it is presented to the cystic duct.
Figure 10:
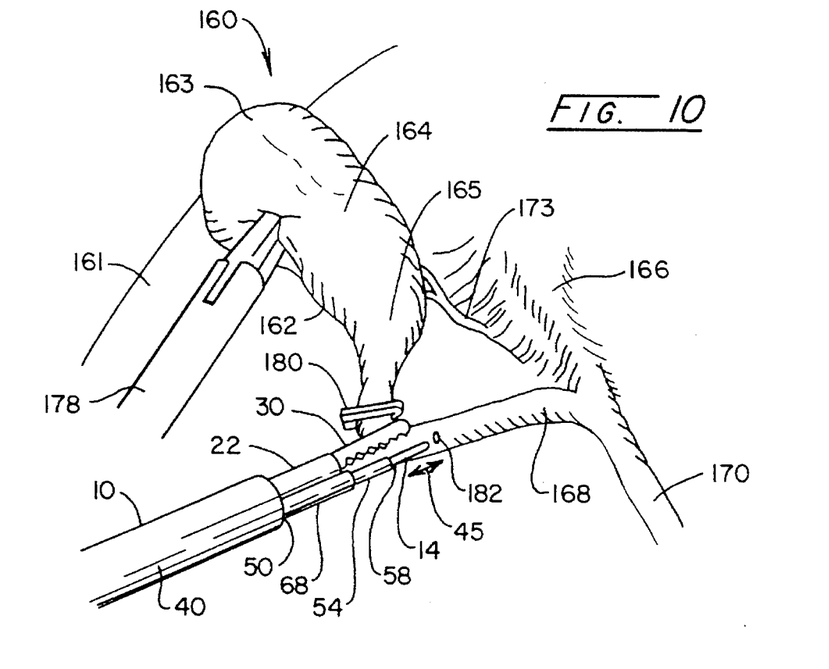
FIG. 10 is an enlarged perspective view of the continuing laparoscopic surgical procedure of FIG. 6 showing the expressing of the catheter from the output end of the guide instrument of FIG. 1.

Proceeding to FIG. 9, with instrument 10 and duct 168 having been placed in general alignment, duct 168 may be partially transected with microscissors 176 to form an opening, 182, through which a catheter may be inserted. Advantageously, and as is shown at 60, catheter cannula 54 may be extended from ! the output end 50 of catheter channel 44 and into contact with duct 168 to indicated to the surgeon where along its length duct 168 should be transected. With duct 168 transected, its cannulation may commence as is shown in FIG. 10 at 45 with the expression of catheter 14 from the output end 58 of catheter cannula 54. As catheter 14 is of a relatively thin-walled and flexible construction, it is supported as it is presented to opening 182 by the extended cannula 54.

Figure 11:
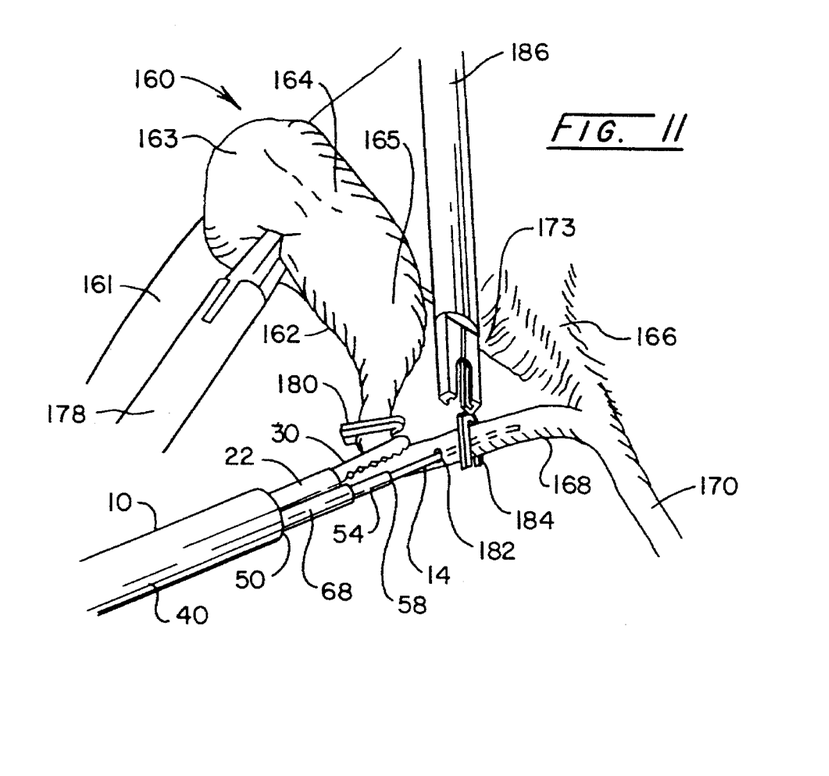
FIG. 11 is an enlarged perspective view of the continuing laparoscopic surgical procedure of FIG. 6 showing the insertion of the catheter into the cystic duct for its cannulation.

Lastly, as is depicted in FIG. 11, following its insertion into opening 182, the catheter 14 expressed from the output end 58 of cannula 54 may be secured within duct 168 with a second surgical clip, 184, which is applied by means of clip applicator 186. With catheter 14 secured in cystic duct 168, cholangiograms may be obtained in a conventional manner by delivering a barium fluid or the like through catheter 14 and into duct 168. Any ductal stones detected by the cholangiograms may be removed using conventional retrieval techniques. Alternatively, instrument 10 again may be employed to deliver a cholangioscope through channel 44 and into duct 168 for exploration of the common bile duct 170 and the extraction of any stones therefrom. Following the extraction of any ductal stones, cystic duct 168 may be clipped with additional surgical clips (not shown) applied to near its junction with hepatic duct 166, and then divided between those clips and clip 180. With cystic duct 168 transected, cystic artery 173 may be divided using a double clip ligation procedure similar to that described for the transection of cystic duct 168. Following the transection of duct 168 and artery 173, gallbladder 162 may be completely dissected from liver 161, the and the procedure may conclude with the extraction of gallbladder 162 through one of the lateral ports 156 or 158 shown in FIG. 4.

As it is anticipated that certain changes may be made in the present invention without departing from the precepts herein involved, it is intended that all matter contained in the foregoing description shall be interpreted as illustrative and not in a limiting sense.

What is claimed:

1. A guide instrument for cannulating a biliary duct with a flexible catheter as part of a laparoscopic cholangiographic surgical procedure, said instrument comprising:

(a) a grasping forceps component comprising:
        (i) an elongate shaft extending along a longitudinal axis between a first and a second end;
        (ii) a pair of jaws positioned at said first end of said shaft and mutually pivotally coupled thereat for movement between an opened and a closed orientation for selectively grasping said duct; and
        (iii) an actuator positioned at said second end of said shaft and coupled in a drive relationship with said jaws for moving said jaws between said opened orientation and said closed orientation; and (b) an elongate, generally cylindrical guide tube slidably supported along said elongate shaft, having an internal catheter channel extending therethrough, said catheter channel having a central axis spaced radially from said longitudinal axis and extending between an input end for receiving the catheter and an output end for expressing the catheter from said guide tube, said guide tube being rotatable about said longitudinal axis to define with the central axis of said catheter channel a first confrontation radius for presenting the catheter expressed from the output end of said catheter channel to said biliary duct at a confrontation angle effective for cannulating said duct as said duct is grasped between the jaws of said grasping forceps component.

2. The guide instrument of claim 1 wherein said guide tube is formed as having an internal support channel extending therethrough, said shaft of said grasping forceps component being received within said support channel for slidably rotatably supporting said guide tube on said shaft.

3. The guide instrument of claim 1 further comprising an elongate catheter cannula slidably received within said catheter channel, said cannula having an internal diametric extent configured to slidably receive said catheter therethrough and extending between an input end for supporting the catheter received at the input end of said catheter channel and an output end for supporting the catheter expressed from the output end of said catheter channel, said cannula being extensible from the output end of said catheter channel for supporting the catheter as it is presented to said biliary duct.

4. The guide instrument of claim 3 wherein the output end of said catheter cannula is acutely angled with respect to the central axis of said cannula to describe a generally arcuate locus when said cannula is rotated about its central axis within said catheter channel, said arcuate locus defining a second confrontation radius about said central axis for presenting the catheter expressed from the output end of said catheter channel to said biliary duct at said confrontation angle effective for cannulating said duct.

5. The guide instrument of claim 4 wherein the output end of said catheter cannula is formed has having a generally elliptically-shaped opening.

6. The guide instrument of claim 3 further comprising a guide sleeve having an outer diametric extent configured to be received by said catheter channel and an inner diametric extent configured to receive said catheter cannula, said guide sleeve being slidably received within said catheter channel and said catheter cannula being slidably received within said guide sleeve.

7. The guide instrument of claim 6 further comprising a first elastomeric end cap disposed about the input end of said guide tube, said first elastomeric end configured to receive said guide sleeve and said elongate shaft of said grasping forceps component therethrough for hermetically sealing said guide tube.

8. The guide instrument of claim 7 further comprising a second elastomeric end cap disposed about the input end of said catheter cannula, said second elastomeric end cap configured to receive the catheter therethrough for effecting a hermetic seal between the catheter and said cannula.

9. The guide instrument of claim 8 further comprising at least one auxiliary channel internally extending through said guide tube between an input end and an output end, said auxiliary channel having an inner diametric extent configured to slidably receive a laparoscopic surgical instrument.

10. A guide instrument for presenting a second instrument to a biliary duct as part of a laparoscopic cholangiographic surgical procedure, said instrument comprising:

(a) a gasping forceps component comprising:
        (i) an elongate shaft extending along a longitudinal axis between a first and a second end;
        (ii) a pair of jaws being positioned at said first end of said shaft and mutually pivotally coupled thereat for movement between an opened and a closed orientation for selectively grasping said duct;
        (iii) an actuator positioned at said second end of said shaft and coupled in a drive relationship with said jaws for moving said jaws between said open orientation and said closed orientation; and (b) an elongate, generally cylindrical guide tube slidably supported along said longitudinal axis of said elongate shaft having an internal instrument channel therethrough, said instrument channel having a central axis spaced radially from said longitudinal axis and extending between an input end for receiving the second instrument and an output end for expressing the second instrument from said guide tube, said guide tube being rotatable about said longitudinal axis to define with the central axis of said instrument channel a first confrontation radius for presenting the second instrument expressed from the output end of said instrument channel to said biliary duct at a select confrontation angle as said duct is grasped between the jaws of said grasping forceps component.

11. The guide instrument of claim 10 wherein said guide tube is formed as having an internal support channel extending therethrough, said shaft of said grasping forceps component being received within said support channel for slidably rotatably supporting said guide tube on said shaft.

12. The guide instrument of claim 10 further comprising a guide sleeve having an outer diametric extent configured to be received by said instrument channel and an inner diametric extent configured to receive said second instrument, said guide sleeve being slidably received within said instrument channel and said second instrument being slidably received within said guide sleeve.

13. The guide instrument of claim 12 further comprising a first elastomeric end cap disposed about the input end of said guide tube, said first elastomeric end configured to receive said guide sleeve and said elongate shaft of said gasping forceps component therethrough for hermetically sealing said guide tube.

14. The guide instrument of claim 13 further comprising a second elastomeric end cap disposed about the input end of said guide sleeve, said second elastomeric end cap configured to receive said second instrument therethrough for effecting a hermetic seal between said guide sleeve and said second instrument.

15. The guide instrument of claim 10 further comprising at least one auxiliary channel internally extending through said guide tube between an input end and an output end, said auxiliary channel having an inner diametric extent configured to slidably receive a third laparoscopic surgical instrument.

16. The guide instrument of claim 10 wherein said second instrument is a cholangioscope.

17. A method for cannulating a biliary duct with a flexible catheter as part of a laparoscopic cholangiographic surgical procedure, said method comprising the steps of:

(a) providing a guide instrument comprising:
  (i) a grasping forceps component comprising:
    an elongate shaft extending along a longitudinal axis between a first and a second end;
    a pair of jaws positioned at said first end of said shaft and mutually pivotally coupled thereat for movement between an opened and a closed orientation for selectively grasping said duct; and
    an actuator positioned at said second end of said shaft and coupled in a drive relationship with said jaws for moving said jaws between said opened orientation and said closed orientation; and
  (ii) an elongate, generally cylindrical guide tube slidably supported on said longitudinal axis of said elongate shaft having an internal catheter channel therethrough, said catheter channel having a central axis spaced radially from said longitudinal axis and extending between an input end for receiving the catheter and an output end for expressing the catheter from said guide tube, said guide tube being rotatable about said longitudinal axis to define with the central axis of said catheter channel a first confrontation radius for presenting the catheter expressed from the output end of said catheter channel to said biliary duct at a confrontation angle effective for cannulating said duct as said duct is grasped between the jaws of said gasping forceps component;

(b) grasping said biliary duct between the jaws of said grasping forceps component;

(c) directing the catheter of said guide instrument through the catheter channel of the guide tube to express the catheter from the output end thereof;

(d) rotating the guide tube about the longitudinal axis of the elongate shaft of the gasping forceps component to present the catheter expressed from the output end of said guide tube to said biliary duct at a confrontation angle effective for cannulating said duct; and (e) inserting the catheter into said duct for its cannulation.

18. The method of claim 17 wherein said guide instrument is provided as further comprising an elongate catheter cannula slidably received within said catheter channel, said cannula having an internal diametric extent configured to slidably receive said catheter therethrough and extending between an input .end for supporting the catheter received at the input end of said catheter channel and an output end for supporting the catheter expressed from the output end of said catheter channel, said cannula being extensible from the output end of said catheter channel for supporting the catheter as it is presented to said biliary duct.

19. The method of claim 18 further comprising the step of extending said catheter cannula from the output end of said catheter channel to said biliary duct to support the catheter as it is presented to said biliary duct.

20. The method of claim 19 wherein said guide instrument is provided as further comprising a guide sleeve having an outer diametric extent configured to be received by said catheter channel and an inner diametric extent configured to receive said catheter cannula, said guide sleeve being slidably received within said catheter channel and said catheter cannula being slidably received within said guide sleeve.

21. The method of claim 20 further comprising the step of extending said guide sleeve from the output end of said catheter channel for supporting the catheter cannula as it is extended to said biliary duct.

22. The method of claim 18 wherein the output end of said catheter cannula of said guide instrument is provided as being acutely angled with respect to the central axis of said cannula to describe a generally arcuate locus when said cannula is rotated about its central axis within said catheter channel, said arcuate locus defining a second confrontation radius about said central axis for presenting the catheter expressed from the output end of said catheter channel to said biliary duct at said confrontation angle effective for cannulating said duct.

23. The method of claim 22 further comprising the step of rotating said catheter cannula about its central axis to present the catheter expressed from the output end of said guide tube to said biliary duct at said confrontation angle effective for cannulating said duct.

* * * * *